US008440864B2

(12) United States Patent
Buchanan et al.

(10) Patent No.: US 8,440,864 B2
(45) Date of Patent: May 14, 2013

(54) PROCESS FOR PRODUCING SEC-BUTYLBENZENE

(75) Inventors: John S. Buchanan, Lambertville, NJ (US); Jon E. R. Stanat, Westhampton Beach, NY (US); James R. Lattner, Laporte, TX (US); Jane C. Cheng, Bridgewater, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 181 days.

(21) Appl. No.: 13/060,773

(22) PCT Filed: Aug. 4, 2009

(86) PCT No.: PCT/US2009/052630
§ 371 (c)(1),
(2), (4) Date: Feb. 25, 2011

(87) PCT Pub. No.: WO2010/042268
PCT Pub. Date: Apr. 15, 2010

(65) Prior Publication Data
US 2011/0152577 A1    Jun. 23, 2011

Related U.S. Application Data

(60) Provisional application No. 61/104,280, filed on Oct. 10, 2008.

(51) Int. Cl.
*C07C 45/00* (2006.01)
*C07C 37/08* (2006.01)
*C07C 2/08* (2006.01)
*C07C 2/04* (2006.01)

(52) U.S. Cl.
USPC ........... 568/385; 568/768; 568/798; 585/461; 585/486

(58) Field of Classification Search .................. 568/385, 568/768, 798; 585/461, 486
See application file for complete search history.

(56) References Cited

U.S. PATENT DOCUMENTS

| | | | |
|---|---|---|---|
| 2,276,199 A | 3/1942 | Kassel | |
| 2,282,469 A | 5/1942 | Frolich | |
| 2,584,103 A | 2/1952 | Pines et al. | |
| 3,325,465 A | 6/1967 | Jones et al. | |
| 3,819,735 A | 6/1974 | Argento et al. | |
| 4,051,191 A | 9/1977 | Ward | |
| 4,058,576 A | 11/1977 | Chang et al. | |
| 4,144,138 A | 3/1979 | Rao et al. | |
| 4,454,367 A | 6/1984 | Sakurada et al. | |
| 4,471,154 A | 9/1984 | Franklin | |
| 4,490,565 A | 12/1984 | Chang et al. | |
| 4,490,566 A | 12/1984 | Chang et al. | |
| 4,822,921 A | 4/1989 | Knifton et al. | |
| 4,891,458 A | 1/1990 | Innes et al. | |
| 4,956,514 A | 9/1990 | Chu | |
| 4,992,606 A | 2/1991 | Kushnerick et al. | |
| 5,059,736 A | 10/1991 | Tamura et al. | |
| 5,065,794 A | 11/1991 | Cheung | |
| 5,081,323 A | 1/1992 | Innes et al. | |
| 5,091,590 A | 2/1992 | Harandi et al. | |
| 5,177,283 A | 1/1993 | Ward | |
| 5,183,945 A | 2/1993 | Stibrany et al. | |
| 5,298,667 A | 3/1994 | Iwanaga et al. | |
| 5,336,820 A | 8/1994 | Owen et al. | |
| 5,368,691 A | 11/1994 | Asselineau et al. | |
| 5,371,310 A | 12/1994 | Bennett et al. | |
| 5,387,721 A | 2/1995 | Kruse et al. | |
| 5,401,429 A | 3/1995 | Flynn et al. | |
| 5,557,024 A | 9/1996 | Cheng et al. | |
| 5,723,710 A | 3/1998 | Gajda et al. | |
| 5,910,528 A | 6/1999 | Falicoff et al. | |
| 5,922,920 A | 7/1999 | Bond et al. | |
| 6,002,057 A | 12/1999 | Hendriksen et al. | |
| 6,051,521 A | 4/2000 | Cheng et al. | |
| 6,169,215 B1 | 1/2001 | Levin et al. | |
| 6,169,216 B1 | 1/2001 | Levin et al. | |
| 6,274,783 B1 | 8/2001 | Gildert et al. | |
| 6,275,783 B1 | 8/2001 | Okamura | |
| 6,297,406 B1 | 10/2001 | Levin et al. | |
| 6,410,804 B1 | 6/2002 | Levin et al. | |
| 6,440,886 B1 | 8/2002 | Gajda et al. | |
| 6,500,999 B2 | 12/2002 | Di Girolamo et al. | |
| 6,657,090 B2 | 12/2003 | Rix et al. | |
| 6,720,462 B2 | 4/2004 | Kuhnle et al. | |
| 6,914,166 B2 | 7/2005 | Dakka et al. | |
| 7,112,711 B2 | 9/2006 | Mathys et al. | |

(Continued)

FOREIGN PATENT DOCUMENTS

| | | |
|---|---|---|
| DE | 2 300 903 | 8/1973 |
| DE | 35 42 171 | 6/1987 |
| EP | 0 390 596 | 10/1990 |
| EP | 0 736 584 | 10/1996 |
| EP | 0 994 088 | 4/2000 |
| EP | 1 088 809 | 4/2001 |
| GB | 797986 | 7/1958 |
| JP | 2002-282698 | 10/2002 |
| SU | 417405 | 8/1974 |

(Continued)

OTHER PUBLICATIONS

Hauge et al., "Oligomerization of Isobutene Over Solid Acid Catalysts", Catalysis Today, 2005, vol. 100, pp. 436-466.
Isakov et al., "Catalytic Properties of Palladium-Zeolite Systems in the Synthesis of Sec-Butylbenzene From Benzene and Ethylene", Inst. Org. Khim, im. N. D. Zelinskogo, Moscow, Russia, Neftekhimiya, 1994, vol. 34, No. 2, pp. 151-170 (Abstract Only; XP002317126).

(Continued)

*Primary Examiner* — Sikarl Witherspoon
(74) *Attorney, Agent, or Firm* — Anthony G. Boone; Jamie L. Sullivan; Siwen Chen

(57) ABSTRACT

In a process for producing sec-butylbenzene, a $C_4$ olefinic hydrocarbon feedstock comprising isobutene and at least one n-butene is contacted with methanol and/or water in the presence of an acid catalyst to selectively oxygenate isobutene to produce an effluent stream rich in n-butene and containing less isobutene than the feedstock. The effluent stream is then contacted with benzene under alkylation conditions and in the presence of an alkylation catalyst to produce alkylation stream comprising sec-butylbenzene.

25 Claims, No Drawings

U.S. PATENT DOCUMENTS

| | | | |
|---|---|---|---|
| 2002/0078622 | A1 | 6/2002 | Rix et al. |
| 2003/0083527 | A1 | 5/2003 | Kuhnle et al. |
| 2007/0213576 | A1 | 9/2007 | Brown et al. |
| 2008/0086018 | A1 | 4/2008 | Cheng et al. |

FOREIGN PATENT DOCUMENTS

| | | |
|---|---|---|
| SU | 265349 | 10/1976 |
| SU | 1245564 | 7/1986 |
| WO | 91/18851 | 12/1991 |
| WO | 2007/094938 | 8/2007 |

OTHER PUBLICATIONS

Isakov et al., "Study of Polyfunctional Zeolite Catalysts. Communication 2. Formation of a Catalyst for Synthesis Off Sec-Butylbenzene Prepared From Nickel Acetylacetonate and Cay Zeolite", Inst. Org. Khim. im. Zelinskogo, Moscow, USSR, Izv. Akad Nauk SSSR, Ser. Khim., 1976, vol. 3, pp. 498-504 (Abstract Only).

Marchionna et al., "Light Olefins Dimerization to High Quality Gasoline Components", Catalysis Today, 2001, vol. 65, pp. 397-403.

Minachev et al., "Study of the Nature of Bifunctional Catalysts for the Synthesis of Sec-Butylbenzene From Ethylene and Benzene", Inst. Org. Khim, im. Zelinskogo, Moscow, USSR, Geterog. Katal., 1979, Pt. 2, pp. 485-492 (Abstract Only).

Minachev et al., "Alkylation of Benzene by Ethylene on Catalysts Produced From Synthetic Zeolites Ultrasil", Inst. Org. Khim, im. Zelinskogo, Moscow, USSR, Neftekhimiya, 1988, vol. 28, No. 2, pp. 151-158 (Abstract Only: XP-002317128).

Minachev et al., "Bifunctional Catalysts for the Alkylation of Aromatic Compounds by Ethylene", USSR, Lektsii-Vses, Shk. Katal, 1981, vol. 2, pp. 76-111 (Abstract Only: XP-002317129).

Ohkubo et al., "A Kinetic Study on the Homogeneous Liquid-Phase Oxidation of Cumene in the Presence of Triphenylsulfonium Chloride", Bull. Chem. Soc., Japan, 1969, vol. 42, No. 7, pp. 1800-1806.

Sachanen et al., "High-Temperature Alkylation of Aromatic Hydrocarbons", Ind. Eng. Chem., vol. 33, No. 12, 1941, pp. 1540-1544.

Sidorov et al., "Alkylation of Benzene With Olefins", Sernaya Kislota Protsessakh Neftekhim, 1975, pp. 172-177.

Yen, "Phenol", Process Economics Report No. 22B, Stanford Research Institute, Dec. 1977, pp. 113-124, 261 and 263.

PROCESS FOR PRODUCING SEC-BUTYLBENZENE

CROSS REFERENCE TO RELATED APPLICATIONS PRIORITY CLAIM

This application is a National Stage Application of International Application No. PCT/US2009/052630, filed Aug. 4, 2009, which claims the benefit of prior U.S. provisional application Ser. No. 61/104,280, filed Oct. 10, 2008, both of which are hereby incorporated by reference in their entirety.

CROSS-REFERENCE TO RELATED APPLICATIONS

This application is related to U.S. Pat. Nos. 6,914,166; 7,799,956; 7,834,218; and U.S. patent application Ser. No. 12/674,443, filed Oct. 2, 2008.

FIELD

The present invention relates to a process for producing sec-butylbenzene and for converting the sec-butylbenzene to phenol and methyl ethyl ketone.

BACKGROUND

Phenol and methyl ethyl ketone are important products in the chemical industry. For example, phenol is useful in the production of phenolic resins, bisphenol A, $\epsilon$-caprolactam, adipic acid, alkyl phenols, and plasticizers, whereas methyl ethyl ketone can be used as a lacquer, a solvent and for dewaxing of lubricating oils.

The most common route for the production of methyl ethyl ketone is by dehydrogenation of sec-butyl alcohol (SBA), with the alcohol being produced by the acid-catalyzed hydration of butenes. For example, commercial scale SBA manufacture by reaction of butylene with sulfuric acid has been accomplished for many years via liquid/liquid extraction and gas/liquid absorption.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene relative to that for butenes is likely to increase, due to a developing shortage of propylene. Thus, a process that uses butenes instead of propylene as feed and co-produces methyl ethyl ketone rather than acetone may be an attractive alternative route to the production of phenol.

It is known that phenol and methyl ethyl ketone can be co-produced by a variation of the Hock process in which sec-butylbenzene is oxidized to obtain sec-butylbenzene hydroperoxide and the peroxide decomposed to the desired phenol and methyl ethyl ketone. An overview of such a process is described in pages 113-121 and 261-263 of Process Economics Report No. 22B entitled "Phenol", published by the Stanford Research Institute in December 1977.

In addition, it is known that sec-butylbenzene can be produced by alkylating benzene with n-butenes over an acid catalyst. For example, in our International Patent Publication No. WO06/015826, we have described a process for producing phenol and methyl ethyl ketone, in which benzene is initially contacted with a $C_4$ alkylating agent under alkylation conditions with a catalyst comprising zeolite beta or a molecular sieve of the MCM-22 family to produce an alkylation effluent comprising sec-butylbenzene. The sec-butylbenzene is then oxidized to produce a hydroperoxide and the hydroperoxide is decomposed to produce phenol and methyl ethyl ketone.

Although the chemistry involved in the alkylation of benzene with butenes is very similar to that for ethylbenzene and cumene production, as the carbon number of the alkylating agent increases, the number of product isomers also increases. For example, ethylbenzene has one isomer, propylbenzene has two isomers (cumene and n-propylbenzene), and butylbenzene has four isomers (n-, iso-, sec-, and tert-butylbenzene). For sec-butylbenzene production, it is important to minimize n-, iso-, tert-butylbenzene, and phenyl-butenes by-product formation since these by-products, have boiling points very close to sec-butylbenzene and hence are difficult to separate from sec-butylbenzene by distillation (see table below).

| Butylbenzene | Boiling Point, ° C. |
| --- | --- |
| t-Butylbenzene | 169 |
| i-Butylbenzene | 171 |
| s-Butylbenzene | 173 |
| n-Butylbenzene | 183 |

Moreover, iso-butylbenzene and especially tert-butylbenzene are known to be inhibitors to the oxidation of sec-butylbenzene to the corresponding hydroperoxide, a necessary next step for the production of methyl ethyl ketone and phenol. However, although by-product formation can be minimized by using a pure n-butene feed, in practice it is desirable to employ more economical butene feeds, such as Raffinate-1, to produce sec-butylbenzene. A typical Raffinate-1 contains up to 2% butadiene and more than 5% isobutene. With this increased isobutene in the feed, a higher by-product make is expected even with a highly selective alkylation catalyst. Moreover, butadiene, if present, poses a significant problem since its alkylation product, phenyl-butene, is an oxidation inhibitor and could react with another benzene to form diphenybutane byproduct.

There is therefore a need to provide a process for the production of sec-butylbenzene by alkylation of benzene using a mixed $C_4$ olefin feed, such as Raffinate-1, in which the formation of undesirable by-products is significantly reduced by subjecting the feed to a pretreatment process that selectively reduces the level of isobutene and, where present, butadiene in the feed without excessive loss of valuable n-butenes.

International Patent Publication No. WO06/015826 discloses that isobutene in a mixed $C_4$ olefin feed can be removed by dimerization or reaction with methanol to produce MTBE, prior to use of the feed in the alkylation of benzene to produce sec-butylbenzene. In practice, however, with Raffinate-1 and similar unprocessed $C_4$ olefin feeds, we have found that using water and/or methanol as the reactive species, it is difficult in a single stage of contacting to secure sufficient conversion of isobutene to reduce the level of this isomer sufficiently to prevent significant iso-butylbenzene and tert-butylbenzene production in the subsequent alkylation step.

SUMMARY

Accordingly, in one aspect the invention resides in a process for producing sec-butylbenzene, the process comprising:

(a) contacting a $C_4$ olefinic hydrocarbon feedstock comprising isobutene and at least one n-butene with methanol and/or water in the presence of an acid catalyst and under conditions effective to selectively oxygenate isobutene and produce a first effluent containing less isobutene than the feedstock;

(b) separating said first effluent into a first heavy fraction rich in oxygenated isobutene and a first light fraction rich in said at least one n-butene and isobutene;

(c) contacting said first light fraction with additional methanol and/or water in the presence of an acid catalyst and under conditions effective to selectively oxygenate isobutene and produce a second effluent containing less isobutene than the first light fraction;

(d) separating said second effluent into a second heavy fraction rich in oxygenated isobutene and a second light fraction rich in said at least one n-butene and isobutene; and (e) contacting said second light fraction with benzene under alkylation conditions and in the presence of an alkylation catalyst to produce a third effluent comprising sec-butylbenzene.

Conveniently, said $C_4$ olefinic hydrocarbon feedstock comprises more than 5 wt % isobutene, for example 10 to 60 wt % isobutene, said first light fraction comprises from about 1 to about 5 wt % isobutene and said second light fraction contains less than 2000 ppm isobutene, such as less than 1000 ppm isobutene, for example less than 200 ppm isobutene.

Conveniently, at least one of said separating (b) and said separating (d) comprises distillation. In one embodiment, steps (a) and (b) and/or steps (c) and (d) occur substantially simultaneously, such as by catalytic distillation.

In one embodiment, the two stages of contacting (a) and (c) take place in a single integrated process unit. In another embodiment, the two stages of contacting (a) and (c) take place in two distinct processing units.

Conveniently, said acid catalyst in each of (a) and (c) is independently selected from at least one of an ion exchange resin, phosphoric acid, a heteropolyacid and a zeolite. Typically, the conditions employed in each of (a) and (c) comprise a temperature of about 30° C. to about 160° C., a pressure of about 50 to about 500 psig (445 to 3550 kPa), and an LHSV of about 2 to about 20 $hr^{-1}$.

Conveniently, said $C_4$ olefinic hydrocarbon feedstock further comprises butadiene and the process includes selective hydrogenation of said butadiene to butenes. In one embodiment, said $C_4$ olefinic hydrocarbon feedstock further comprises up to 1 wt % butadiene and said selective hydrogenation produces a product containing less than 5000 ppm butadiene. Said selective hydrogenation may be conducted on said $C_4$ olefinic hydrocarbon feedstock prior to said contacting (a) or on said second light fraction prior to said contacting (e).

In a further aspect, the invention resides in a process for producing phenol and methyl ethyl ketone, the process comprising:

(a) contacting a $C_4$ olefinic hydrocarbon feedstock comprising butadiene, isobutene and at least one n-butene with hydrogen in the presence of a hydrogenation catalyst to selectively hydrogenate said butadiene and produce a hydrogenation product;

(b) contacting at least part of said hydrogenation product with methanol and/or water in the presence of an acid catalyst and under conditions effective to selectively oxygenate said isobutene and produce a first effluent;

(c) separating said first effluent into a first heavy fraction rich in oxygenated isobutene and a first light fraction rich in said at least one n-butene and isobutene;

(d) contacting said first light fraction with additional methanol and/or water in the presence of an acid catalyst and under conditions effective to selectively oxygenate isobutene and produce a second effluent containing less isobutene than the first light fraction;

(e) separating said second effluent into a second heavy fraction rich in oxygenated isobutene and a second light fraction rich in said at least one n-butene and isobutene;

(f) contacting said second light fraction with benzene under alkylation conditions and in the presence of an alkylation catalyst to produce a third effluent comprising sec-butylbenzene;

(g) oxidizing the sec-butylbenzene from said third effluent to produce sec-butylbenzene hydroperoxide; and (h) cleaving the sec-butylbenzene hydroperoxide from (f) to produce phenol and methyl ethyl ketone.

In yet a further aspect, the invention resides in a process for producing phenol and methyl ethyl ketone, the process comprising:

(a) contacting a $C_4$ olefinic hydrocarbon feedstock comprising butadiene, isobutene and at least one n-butene with methanol and/or water in the presence of an acid catalyst and under conditions effective to selectively oxygenate said isobutene and produce a first effluent containing less isobutene than the feedstock;

(b) separating said first effluent into a first heavy fraction rich in oxygenated isobutene and a first light fraction rich in said at least one n-butene and isobutene;

(c) contacting said first light fraction with additional methanol and/or water in the presence of an acid catalyst and under conditions effective to selectively oxygenate isobutene and produce a second effluent containing less isobutene than the first light fraction;

(d) separating said second effluent into a second heavy fraction rich in oxygenated isobutene and a second light fraction rich in said at least one n-butene and said isobutene;

(e) contacting said second light fraction with hydrogen in the presence of a hydrogenation catalyst to selectively hydrogenate said butadiene and produce a hydrogenation product;

(f) contacting at least part of said hydrogenation product with benzene under alkylation conditions and in the presence of an alkylation catalyst to produce a third effluent comprising sec-butylbenzene;

(g) oxidizing the sec-butylbenzene from said third effluent to produce sec-butylbenzene hydroperoxide; and (h) cleaving the sec-butylbenzene hydroperoxide from (f) to produce phenol and methyl ethyl ketone.

Conveniently, said alkylation catalyst comprises at least one molecular sieve of the MCM-22 family.

DETAILED DESCRIPTION OF THE EMBODIMENTS

Described herein is a process for producing sec-butylbenzene by alkylating benzene with a $C_4$ olefinic hydrocarbon feedstock, such as Raffinate-1, which contains isobutene, typically in excess of 5 wt %, and optionally butadiene, in addition to one or more n-butenes. Since the isobutene will tend to alkylate the benzene to produce the undesirable co-boilers iso-butylbenzene and tert-butylbenzene, the present process includes an initial multi-stage pretreatment of the feedstock with water and/or methanol so as to selectively remove the isobutene in the feedstock. Depending on the reagent employed the reaction with the water and/or methanol oxygenates the isobutene to an alcohol or ether, which can be removed from the product by distillation and used as, for example, a fuel or a solvent. Where the feedstock also includes butadiene, the pretreatment can also include selective hydrogenation of the butadiene to butenes, especially butene-2, which can be used to produce additional sec-butylbenzene.

Using the present pretreatment process, a $C_4$ olefinic hydrocarbon feedstocks containing in excess of 5 wt % isobutene and up to 1 wt % butadiene can be converted to a product containing less than 2000 ppm, such as less than 1000 ppm, for example less than 200 ppm, isobutene and less than 5000 ppm, such as less than 1000 ppm, for example less than 200 ppm, butadiene. Such a product represents an excellent feed for the alkylation of benzene to produce sec-butylbenzene in high yield.

Olefinic Hydrocarbon Feedstock

Any $C_4$ olefinic hydrocarbon feedstock containing isobutene and at least one n-butene can be used in the present process, although the process is particularly applicable to feedstocks containing significant amounts isobutene, and optionally butadiene, in addition to linear butenes, namely butene, cis-butene, trans-butene or mixtures thereof. Such olefinic $C_4$ hydrocarbon mixtures can be obtained by steam cracking of ethane, propane, butane, LPG and light naphthas, catalytic cracking of naphthas and other refinery feedstocks and by conversion of oxygenates, such as methanol, to lower olefins. The present pretreatment process then serves to reduce the isobutene concentration and, if present, the butadiene concentration of the olefinic $C_4$ hydrocarbon mixture.

For example, one olefinic $C_4$ hydrocarbon stream generally available in any refinery employing steam cracking to produce olefins is Raffinate-1, the product remaining after solvent extraction or hydrogenation to remove butadiene from a crude steam cracked butene stream. Generally, Raffinate 1 has a composition within the weight ranges indicated in Table 1 below.

TABLE 1

| | | Raffinate 1 | |
| --- | --- | --- | --- |
| Component | Crude $C_4$ stream | Solvent Extraction | Hydrogenation |
| Butadiene | 30-85% | 0-2% | 0-2% |
| C4 acetylenes | 0-15% | 0-0.5% | 0-0.5% |
| Butene-1 | 1-30% | 20-50% | 50-95% |
| Butene-2 | 1-15% | 10-30% | 0-20% |
| Isobutene | 0-30% | 0-55% | 0-35% |
| N-butane | 0-10% | 0-55% | 0-10% |
| Isobutane | 0-1% | 0-1% | 0-1% |

Other refinery mixed $C_4$ streams, such as those obtained by catalytic cracking of naphthas and other refinery feedstocks, typically have the following composition:

| | |
| --- | --- |
| Propylene | 0-2 wt % |
| Propane | 0-2 wt % |
| Butadiene | 0-5 wt % |
| Butene-1 | 5-20 wt % |
| Butene-2 | 10-50 wt % |
| Isobutene | 5-25 wt % |
| Iso-butane | 10-45 wt % |
| n-Butane | 5-25 wt % |

$C_4$ hydrocarbon fractions obtained from the conversion of oxygenates, such as methanol, to lower olefins more typically have the following composition:

| | |
| --- | --- |
| Propylene | 0-1 wt % |
| Propane | 0-0.5 wt % |
| Butadiene | 0-1 wt % |
| Butene-1 | 10-40 wt % |
| Butene-2 | 50-85 wt % |
| Isobutene | 0-10 wt % |
| n- + iso-butane | 0-10 wt % |

Any one or any mixture of the above $C_4$ hydrocarbon mixtures can be used in the present process.

In addition to other hydrocarbon components, commercial $C_4$ hydrocarbon mixtures typically contain other impurities which could be detrimental to the pretreatment process or the subsequent alkylation process. For example, refinery $C_4$ hydrocarbon streams typically contain nitrogen and sulfur impurities, whereas $C_4$ hydrocarbon streams obtained by oxygenate conversion process typically contain unreacted oxygenates and water. Thus, prior to the pretreatment process, these mixtures may also be subjected to one or more of sulfur removal, nitrogen removal and oxygenate removal. Removal of sulfur, nitrogen, oxygenate impurities is conveniently effected by one or a combination of caustic treatment, water washing, distillation, adsorption using molecular sieves and/or membrane separation. Water is also typically removed by adsorption.

Conveniently, the total feed to the present process contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Although not preferred, it is also possible to employ a mixture of a $C_4$ alkylating agent, as described above, and $C_3$ alkylating agent, such as propylene, as the alkylating agent in the present alkylation process so that the alkylation step produces a mixture of cumene and sec-butylbenzene. The resultant mixture can then be processed through oxidation and cleavage, to make a mixture of acetone and MEK, along with phenol, preferably where the molar ratio of acetone to phenol is 0.5:1, to match the demand for bisphenol-A production.

Feed Pretreatment

An initial step in the present process involves reacting the $C_4$ olefinic hydrocarbon feedstock with water and/or methanol in the presence of an acid catalyst to reduce the level of isobutene in the feedstock to less than 2000 ppm, such as less than 1000 ppm, for example less than 200 ppm. To reduce the isobutene content to such low levels, the oxygenation process is affected in at least 2 stages, conveniently with the first stage being conducted in a fixed bed reactor so as to convert most, typically 94 to 96 wt %, of the isobutene to methyl tert-butyl ether (MTBE) and/or tertiary butanol. The effluent of the first reactor is then subjected to a separation step, for instance, distillation, to produce a heavy fraction rich in oxygenated isobutene, and a light fraction rich in at least one n-butene and in isobutene. This light fraction is fed with additional water and/or methanol to a second reactor, typically a catalytic distillation reactor, whereby the overall isobutene conversion can be increased to at least 99.8 wt %. In addition, by conducting the final oxygenation stage in a catalytic distillation reactor, the unreacted $C_4$ olefins can be separated from the heavier ether and/or alcohol products simultaneously with the oxygenation reaction.

When a stream is described as being "rich" in a specified species, it is meant that the specified species in that stream is enriched (on a weight percentage basis) relative to the effluent stream being separated. For illustration purposes only, a stream rich in oxygenated isobutene in the separation step will have an oxygenated isobutene wt % greater than the effluent stream being separated.

Suitable acid catalysts for use in each oxygenation stage include solid ion exchange resins, phosphoric acid, heteropolyacids and zeolites. Suitable ion exchange resins comprise sulfonated polystyrene, such as a divinyl benzene cross-linked polystyrene matrix containing from about 0.5 to about 20% of copolymerized divinyl benzene. Resins of this nature are manufactured and sold commercially under various trade names such as Dowex® 50, Dowex® M-31, Nalcite®. HCR, Amberlyst® 16 and Amberlyst® 15. The use of this type of catalyst is disclosed, for example, in U.S. Pat. No. 4,144,138, the entire contents of which are incorporated herein by reference.

Other suitable catalysts include kieselguhr impregnated with phosphoric acid as disclosed in U.S. Pat. No. 2,282,469 and titania having phosphoric acid impregnated thereon as disclosed in U.S. Pat. No. 4,822,921. Suitable heteropolyacid catalysts include 12-tungstophosphoric acid and 12-molybdophosphoric acid supported on titania. Zeolite catalysts as disclosed in U.S. Pat. No. 4,058,576 to Chang et al. may also be used. Again, the entire contents of these patents are incorporated herein by reference.

Suitable conditions for each oxygenation stage include a temperature of about 30° C. to about 160° C., a pressure of about 50 to about 500 psig (446 to 3457 kPa) and a liquid hourly space velocity (LHSV) of about 2 to about 20 hr$^{-1}$. In general, lower reaction temperatures give more favorable equilibrium conversion of the isobutene, but the reaction rate declines.

Where the $C_4$ olefinic hydrocarbon feedstock also contain significant quantities of butadiene, the feed pretreatment also includes a butadiene removal step, either before or after the isobutene mitigation step. The butadiene removal can be effected by extractive distillation, but generally is achieved by selective hydrogenation in the presence of a metal catalyst, such as palladium, at a temperature of about 0° C. to about 100° C. and a pressure of about 100 to about 1000 kPa. Typically the butadiene level is reduced to less than 5000 ppm, such as less than 1000 ppm, for example less than 200 ppm.

Alkylation to Produce Sec-ButylBenzene

After pretreatment to reduce the level of isobutene and, if necessary, butadiene, the $C_4$ olefinic hydrocarbon feedstock is fed to one or more alkylation reactors for reaction with benzene to produce sec-butylbenzene.

The alkylation catalyst used in the alkylation process is conveniently a crystalline molecular sieve of the MCM-22 family. The term "MCM-22 family material" (or "material of the MCM-22 family" or "molecular sieve of the MCM-22 family" or "MCM-22 family zeolite"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Molecular sieves of the MCM-22 family are preferred as the alkylation catalyst since they have been found to be highly selective to the production of sec-butylbenzene, as compared with the other butylbenzene isomers. Preferably, the molecular sieve is selected from (a) MCM-49, (b) MCM-56 and (c) isotypes of MCM-49 and MCM-56, such as ITQ-2.

The alkylation catalyst can include the molecular sieve in unbound or self-bound form or, alternatively, the molecular sieve can be combined in a conventional manner with an oxide binder, such as alumina, such that the final alkylation catalyst contains between 2 and 80 wt % sieve.

In one embodiment, the catalyst is unbound and has a crush strength much superior to that of catalysts formulated with binders. Such a catalyst is conveniently prepared by a vapor phase crystallization process, in particular a vapor phase crystallization process that prevents caustic used in the synthesis mixture from remaining in the zeolite crystals as vapor phase crystallization occurs.

Prior to use in the alkylation process, the MCM-22 family zeolite, either in bound or unbound form, may be contacted with water, either in liquid or vapor form, under conditions to improve its sec-butylbenzene selectivity. Although the conditions of the water contacting are not closely controlled, improvement in sec-butylbenzene selectivity can generally be achieved by contacting the zeolite with water at temperature of at least 0° C., such as from about 10° C. to about 50° C., for a time of at least 0.5 hour, for example for a time of about 2 hours to about 24 hours. Typically, the water contacting is conducted so as to increase the weight of the catalyst by 30 to 75 wt % based on the initial weight of the zeolite.

The alkylation conditions conveniently include a temperature of from about 60° C. to about 260° C., for example between about 100° C. and about 200° C., a pressure of 7000 kPa or less, for example from about 1000 to about 3500 kPa, a weight hourly space velocity (WHSV) based on $C_4$ alkylating agent of between about 0.1 and about 50 hr$^{-1}$, for example between about 1 and about 10 hr$^{-1}$, and a molar ratio of benzene to alkylating agent of from about 1 to about 20, preferably about 3 to about 10, more preferably about 4 to about 9.

The reactants can be in either the vapor phase or partially or completely in the liquid phase and can be neat, i.e., free from intentional admixture or dilution with other material, or they can be brought into contact with the zeolite catalyst composition with the aid of carrier gases or diluents such as, for example, hydrogen or nitrogen. Preferably, the reactants are at least partially in the liquid phase.

Using the catalyst and alkylation conditions described above, it is found that the alkylation process is highly selective to sec-butylbenzene. In particular, at a typical benzene conversion rate of 25 wt % and a butene conversion rate greater than 96 wt %, it is found that the alkylated product (i.e., apart from unreacted benzene) generally comprises at least 93 wt %, typically at least 91 wt %, sec-butylbenzene. Depending on the nature of $C_4$ alkylating agent, the alkylated product may contain between about 10 wt % and about 0.01 wt % tert-butylbenzene and between about 0.1 wt % and about 0.01 wt % iso-butylbenzene. Using Raffinate-2 as the $C_4$ alkylating agent, the alkylated product typically contains between about 5 wt % and about 1 wt % tert-butylbenzene and between about 0.2 wt % and about 0.01 wt % iso-butylbenzene.

Although the alkylation step is highly selective towards sec-butylbenzene, the effluent from the alkylation reaction will normally contain some polyalkylated products, as well as unreacted aromatic feed and the desired monoalkylated species. The unreacted aromatic feed is normally recovered by distillation and recycled to the alkylation reactor. The bottoms from the benzene distillation are further distilled to separate monoalkylated product from any polyalkylated products and other heavies. Depending on the amount of polyalkylated products present in the alkylation reaction effluent, it may be desirable to transalkylate the polyalkylated products with additional benzene to maximize the production of the desired monoalkylated species.

Transalkylation with additional benzene is typically effected in a transalkylation reactor, separate from the alkylation reactor, over a suitable transalkylation catalyst, such as a molecular sieve of the MCM-22 family, zeolite beta, MCM-68 (see U.S. Pat. No. 6,014,018), zeolite Y and mordenite. The transalkylation reaction is typically conducted under at least partial liquid phase conditions, which suitably include a temperature of 100 to 300° C., a pressure of 1000 to 7000 kPa, a weight hourly space velocity of 1 to 50 $hr^{-1}$ on total feed, and a benzene/polyalkylated benzene weight ratio of 1 to 10.

Sec-Butyl Benzene Oxidation

The product of the alkylation process described above is intended for use in the production of phenol by the modified Hock process, in which sec-butylbenzene is oxidized to sec-butylbenzene hydroperoxide and the peroxide is cleaved to produce phenol and methyl ethyl ketone. The initial oxidation step is conveniently accomplished by contacting the alkylation product, generally after separation of the unreacted benzene, with an oxygen-containing gas, such as air, in the liquid phase and in the presence of a catalyst. Thus, unlike cumene, atmospheric air oxidation of sec-butylbenzene in the absence of a catalyst is very difficult to achieve. For example, at 110° C. and at atmospheric pressure, sec-butylbenzene is not oxidized, while cumene oxidizes very well under the same conditions. At higher temperature, the rate of atmospheric air oxidation of sec-butylbenzene improves; however, higher temperatures also produce significant levels of undesired by-products.

Suitable sec-butylbenzene catalysts include a water-soluble chelate compound in which multidentate ligands are coordinated to at least one metal from cobalt, nickel, manganese, copper, and iron (See U.S. Pat. No. 4,013,725). More preferably, a heterogeneous catalyst is used. Suitable heterogeneous catalysts are described in U.S. Pat. No. 5,183,945, wherein the catalyst is an oxo (hydroxo) bridged tetranuclear manganese complex and in U.S. Pat. No. 5,922,920, wherein the catalyst comprises an oxo (hydroxo) bridged tetranuclear metal complex having a mixed metal core, one metal of the core being a divalent metal selected from Zn, Cu, Fe, Co, Ni, Mn and mixtures thereof and another metal being a trivalent metal selected from In, Fe, Mn, Ga, Al and mixtures thereof. The entire disclosures of said U.S. patents are incorporated herein by reference.

Other suitable catalysts for the sec-butylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-obenzenedisulphonimide Preferably, the catalyst is N-hydroxyphthalimide. Another suitable catalyst is N,N', N"-thihydroxyisocyanuric acid.

These materials can be used either alone or in the presence of a free radical initiator and can be used as liquid-phase, homogeneous catalysts or can be supported on a solid carrier to provide a heterogeneous catalyst.

Suitable conditions for the sec-butylbenzene oxidation step include a temperature between about 70° C. and about 200° C., such as about 90° C. to about 130° C., and a pressure of about 0.5 to about 20 atmospheres (50 to 2000 kPa). A basic buffering agent may be added to react with acidic by-products that may form during the oxidation. In addition, an aqueous phase may be introduced, which can help dissolve basic compounds, such as sodium carbonate. The per-pass conversion in the oxidation step is preferably kept below 50%, to minimize the formation of byproducts. The oxidation reaction is conveniently conducted in a catalytic distillation unit and the sec-butylbenzene hydroperoxide produced may be concentrated by distilling off the unreacted sec-butylbenzene prior to the cleavage step.

Hydroperoxide Cleavage

The final step in the conversion of the sec-butylbenzene into phenol and methyl ethyl ketone involves cleavage of the sec-butylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2500 kPa, such as about 100 to about 1000 kPa and a liquid hourly space velocity (LHSV) based on the hydroperoxide of about 0.1 to about 100 $hr^{-1}$, preferably about 1 to about 50 $hr^{-1}$. The sec-butylbenzene hydroperoxide is preferably diluted in an organic solvent inert to the cleavage reaction, such as methyl ethyl ketone, phenol or sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid.

A suitable heterogeneous catalyst for use in the cleavage of sec-butylbenzene hydroperoxide includes a smectite clay, such as an acidic montmorillonite silica-alumina clay, as described in U.S. Pat. No. 4,870,217, the entire disclosure of which is incorporated herein by reference.

The invention will now be more particularly described with reference to the following non-limiting, simulated Examples.

Example 1

This is a two-stage MTBE process, where the first stage outlet is at 40° C. with a 10 degree approach to equilibrium and a 1.2:1 MeOH:isobutene molar ratio. The C4s are then separated from the MTBE product, and fed to a second stage reactor. The second stage outlet is 40° C. with a 20 degree approach to equilibrium and 9:1 MeOH:isobutene molar ratio. The final isobutene/linear butene molar ratio is 0.0013, i.e. 0.13% isobutene in the total butenes. The conversion in the first stage is 96%, and the overall conversion after the second stage is 99.8%.

Example 2

This example removes isobutene by reaction with water to form tert-butanol (TBA). Like Example 1, two stages are needed to get high isobutene conversion. The first stage at 50° C. equilibrium temperature achieves 95% conversion at 1.17 $H_2O$:isobutene molar ratio. The TBA is removed by distillation, and the C4s are fed to a second stage reactor. This achieves 99.8% conversion with 50° C. equilibrium temperature. The $H_2O$:isobutene molar ratio is 4.9:1 in the second stage.

Example 3

Comparative

This example attempts to achieve high isobutene conversion in a single stage using methanol. A 10:1 molar ratio of methanol:isobutene at 40° C. equilibrium temperature only achieves 98.9% conversion of isobutene.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing sec-butylbenzene, the process comprising:
    (a) contacting a $C_4$ olefinic hydrocarbon feedstock comprising isobutene and at least one n-butene with methanol and/or water in the presence of an acid catalyst and under conditions effective to selectively oxygenate isobutene and produce a first effluent containing less isobutene than the feedstock;
    (b) separating said first effluent into a first heavy fraction rich in oxygenated isobutene and a first light fraction rich in said at least one n-butene and said isobutene;
    (c) contacting said first light fraction with additional methanol and/or water in the presence of an acid catalyst and under conditions effective to selectively oxygenate isobutene and produce a second effluent containing less isobutene than the first light fraction;
    (d) separating said second effluent into a second heavy fraction rich in oxygenated isobutene and a second light fraction rich in said at least one n-butene and said isobutene; and
    (e) contacting said second light fraction with benzene under alkylation conditions and in the presence of an alkylation catalyst to produce a third effluent comprising sec-butylbenzene.

2. The process of claim 1, wherein said $C_4$ olefinic hydrocarbon feedstock comprises more than 5 wt % isobutene, said first effluent comprises from about 1 to about 5 wt % isobutene and said second effluent contains less than 2000 ppm isobutene.

3. The process of claim 1, wherein said second effluent contains less than 1000 ppm isobutene.

4. The process of claim 2, wherein said second effluent contains less than 200 ppm isobutene.

5. The process of claim 1, wherein at least one of said separating (b) and said separating (d) comprises distillation.

6. The process of claim 1, wherein steps (a) and (b) and/or steps (c) and (d) occur substantially simultaneously.

7. The process of claim 1, wherein steps (a) and (b) and/or steps (c) and (d) are effected by catalytic distillation.

8. The process of claim 1, wherein said acid catalyst in each of (a) and (c) is independently selected from at least one of an ion exchange resin, phosphoric acid, a heteropolyacid and a zeolite.

9. The process of claim 1, wherein the conditions employed in each of (a) and (c) comprise a temperature of about 30° C. to about 160° C., a pressure of about 50 to about 500 psig (445 to 3550 kPa), and an LHSV of about 2 to about 20 $hr^{-1}$.

10. The process of claim 1, wherein said $C_4$ olefinic hydrocarbon feedstock further comprises butadiene and the process includes selective hydrogenation of said butadiene to butenes.

11. The process of claim 10, wherein said $C_4$ olefinic hydrocarbon feedstock further comprises up to 1 wt % butadiene and said selective hydrogenation produces a product containing less than 5000 ppm butadiene.

12. The process of claim 10, wherein said selective hydrogenation is conducted on said $C_4$ olefinic hydrocarbon feedstock prior to said contacting (a).

13. The process of claim 10, wherein said selective hydrogenation is conducted on said second light fraction prior to said contacting (e).

14. The process of claim 10, wherein said selective hydrogenation is conducted in the presence of a palladium-containing catalyst.

15. The process of claim 1, wherein said C4 olefinic hydrocarbon feedstock further comprises butadiene.

16. The process of claim 15, the process further comprising:
    (f) contacting said $C_4$ olefinic hydrocarbon feedstock with hydrogen in the presence of a hydrogenation catalyst to selectively hydrogenate said butadiene prior to said contacting (a).

17. The process of claim 16, the process further comprising:
    (g) oxidizing the sec-butylbenzene from said third effluent to produce sec-butylbenzene hydroperoxide; and
    (h) cleaving the sec-butylbenzene hydroperoxide from (f) to produce phenol and methyl ethyl ketone.

18. The process of claim 15, wherein said $C_4$ olefinic hydrocarbon feedstock comprises up to 1 wt % butadiene and more than 5 wt % isobutene.

19. The process of claim 1, wherein said alkylation catalyst comprises at least one molecular sieve of the MCM-22 family.

20. The process of claim 17, further comprising converting at least part of said phenol to bisphenol A.

21. The process of claim 15, further comprising contacting said second light fraction with hydrogen in the presence of a hydrogenation catalyst to selectively hydrogenate said butadiene and produce a hydrogenation product prior to said contacting (e).

22. The process of claim 21, the process further comprising:
  (f) contacting at least part of said hydrogenation product with benzene under alkylation conditions and in the presence of an alkylation catalyst to produce a third effluent comprising sec-butylbenzene;
  (g) oxidizing the sec-butylbenzene from said third effluent to produce sec-butylbenzene hydroperoxide; and
  (h) cleaving the sec-butylbenzene hydroperoxide from (f) to produce phenol and methyl ethyl ketone.

23. The process of claim 20, wherein said alkylation catalyst comprises at least one molecular sieve of the MCM-22 family.

24. The process of claim 17, wherein said oxidizing (g) is conducted in the presence of an oxidizing catalyst.

25. The process of claim 24, wherein said oxidizing catalyst comprises N-hydroxyphthalimide.

\* \* \* \* \*